United States Patent
Teutenberg et al.

(10) Patent No.: US 12,123,862 B2
(45) Date of Patent: Oct. 22, 2024

(54) METHOD FOR HANDLING MELT SAMPLES IN A STEELWORKS LABORATORY, AND STEELWORKS LABORATORY

(71) Applicants: thyssenkrupp Industrial Solutions AG, Essen (DE); thyssenkrupp AG, Essen (DE)

(72) Inventors: Reinhard Teutenberg, Unna (DE); Alexander Peters, Beckum (DE)

(73) Assignees: thyssenkrupp Polysius GmbH, Beckum (DE); thyssenkrupp AG, Essen (DE)

( * ) Notice: Subject to any disclaimer, the term of this patent is extended or adjusted under 35 U.S.C. 154(b) by 558 days.

(21) Appl. No.: 17/417,152

(22) PCT Filed: Jan. 30, 2020

(86) PCT No.: PCT/EP2020/052371
§ 371 (c)(1),
(2) Date: Jun. 22, 2021

(87) PCT Pub. No.: WO2020/161003
PCT Pub. Date: Aug. 13, 2020

(65) Prior Publication Data
US 2022/0074911 A1    Mar. 10, 2022

(30) Foreign Application Priority Data
Feb. 7, 2019   (DE) ................. 10 2019 103 029.3

(51) Int. Cl.
G01N 35/02    (2006.01)
G01N 19/06    (2006.01)
(Continued)

(52) U.S. Cl.
CPC .......... *G01N 33/205* (2019.01); *G01N 19/06* (2013.01); *G01N 23/223* (2013.01); *G01N 35/02* (2013.01)

(58) Field of Classification Search
CPC .... G01N 33/205; G01N 19/06; G01N 23/223; G01N 35/02; G01N 2035/00782; G01N 1/286
(Continued)

(56) References Cited

U.S. PATENT DOCUMENTS 3,800,996 A * 4/1974 Fuller .................... B23K 37/08
                                                              228/9
4,541,292 A * 9/1985 Clay ....................... G01N 1/125
                                                              73/864.57
(Continued)

FOREIGN PATENT DOCUMENTS

CA    2757559 A1 * 6/2012 .......... C21C 5/4673
CN    101617231 A    12/2009
(Continued)

OTHER PUBLICATIONS

English Translation of International Search Report issued in PCT/EP2020/052371, dated Apr. 20, 2020.
(Continued)

*Primary Examiner* — Robert R Raevis
(74) *Attorney, Agent, or Firm* — hyssenkrupp North America, LLC (57) ABSTRACT

A method for the handling of melt samples in a steelworks laboratory may involve processing and/or analyzing a melt sample in at least one first treatment apparatus and subsequently transporting the melt sample via at least one first transport path to at least one second treatment apparatus where the melt sample is subjected to further processing and/or analysis. As part of the transporting step, the method
(Continued)

may involve clamping the melt sample on a sample carrier so that the sample carrier is transported together with the clamped-in melt sample between the treatment apparatuses and is positioned in the treatment apparatuses for processing and/or analysis.

9 Claims, 8 Drawing Sheets

(51) Int. Cl.
*G01N 23/223* (2006.01)
*G01N 33/205* (2019.01)

(58) Field of Classification Search
USPC .................. 73/863.01, 864.53–864.59, 866; 356/311–318; 324/536
See application file for complete search history.

(56) References Cited

U.S. PATENT DOCUMENTS

| | | | |
|---|---|---|---|
| 2010/0034701 A1 | 2/2010 | Pedrazzini | |
| 2012/0137757 A1 | 6/2012 | Dams et al. | |
| 2017/0015550 A1* | 1/2017 | Martin | C01B 3/0084 |
| 2019/0374937 A1* | 12/2019 | Doets | B01L 3/502 |

FOREIGN PATENT DOCUMENTS

| | | | | | |
|---|---|---|---|---|---|
| CN | 201623016 U | | 11/2010 | | |
| CN | 102564806 A | | 7/2012 | | |
| CN | 203545142 U | | 4/2014 | | |
| CN | 106636607 A | * | 5/2017 | .......... | C21D 10/005 |
| CN | 206862721 U | * | 1/2018 | .............. | G01N 1/28 |
| CN | 108844843 A | * | 11/2018 | .............. | G01N 3/04 |
| CN | 109283003 A | * | 1/2019 | .............. | G01N 1/04 |
| CN | 110595831 A | | 12/2019 | | |
| DE | 10 2006 049 208 A | | 4/2008 | | |
| DE | 10 2008 050 387 A | | 4/2010 | | |
| DE | 10 2009 003 510 A | | 8/2010 | | |
| DE | 10 2010 006 406 A | | 8/2011 | | |
| EP | 0 281 958 A | | 9/1988 | | |
| EP | 0 633 207 A | | 1/1995 | | |
| EP | 1 201 297 A | | 5/2002 | | |
| GB | 1008829 A | | 11/1965 | | |
| JP | 2014139893 | * | 7/2014 | | |
| KR | 2010001312 A | * | 1/2010 | .............. | G01N 3/28 |
| RU | 2397471 C1 | | 8/2010 | | |

OTHER PUBLICATIONS

Anonymous. "Rotary transfer machine—Wikipedia" 1-14 (Oct. 11, 2018). Retrieved from the Internet: https://en.wikipedia.org/wiki/Rotary_transfer_machine. [retrieved on Apr. 20, 2020].

* cited by examiner

METHOD FOR HANDLING MELT SAMPLES IN A STEELWORKS LABORATORY, AND STEELWORKS LABORATORY

CROSS REFERENCE TO RELATED APPLICATIONS

This application is a U.S. National Stage Entry of International Patent Application Serial Number PCT/EP2020/052371, filed Jan. 30, 2020, which claims priority to German Patent Application No. DE 10 2019 103 029.3, filed Feb. 7, 2019, the entire contents of both of which are incorporated herein by reference.

FIELD

The present disclosure generally relates to steelworks laboratories and to methods for handling melt samples in steelworks laboratories.

BACKGROUND

In all phases of steel production, from pig iron production to the finished product, the most modern manufacturing and measuring methods are used. Here, the precise knowledge of the steel composition is an important aspect since the materials properties depend on it, as well as on the manner of processing. The steel composition arises at the beginning of the production process from the starting materials iron ore, coke, the reduction processes and the alloying-in of accompanying elements in the secondary metallurgy. The composition is conventionally determined by means of random samples from the pig iron melt or steel melt by means of X-ray fluorescence analysis (XRF), combustion analysis and also spark emission spectroscopy. The sample preparation has to meet demanding requirements for these methods.

In conventional process control in a steelworks, a sample taken by means of an immersion probe from a steel melt is transported by means of a tube transport system to a steelworks laboratory. Depending on requirements, the sample has to be cooled before further processing and then goes into a milling machine in order to remove the scale layer from the entire surface. The sample which has been freed of scale is subsequently subjected to X-ray fluorescence analysis or optionally analyzed immediately by means of spark emission spectrometry. In addition to spark emission spectrometry, a combustion analysis is carried out on part of the samples in order to determine the carbon and sulfur content. Part of the swarf obtained during milling or by means of other cutting machining methods is usually used for this purpose. In addition, further treatment apparatuses can be present.

The samples are transported by means of a transport system (conveyor belts or rail system) between the individual treatment apparatuses. In addition, transferring the samples to the next treatment apparatuses by means of a robot is known. Each treatment apparatus is usually provided with transfer units which effect transfer of the sample from the transport system into the treatment apparatus, where the samples are positioned and optionally also measured and treated.

A transport system for transporting samples to different treatment apparatuses is known from EP 0 633 207 A1, in which a circumferential transport belt with sample carriers transported thereon is used. The samples are in this case present in a cup which is arranged on a sample carrier. The sample carriers sit on two conveyor belts of the transport belt during transport. Before a treatment apparatus, the sample carrier is stopped by means of a stopping device and lifted together with the cup containing the sample from the transport belt by means of a handling instrument and transferred into the treatment apparatus. After treatment of the sample, the sample carrier together with the cup containing the sample is returned to the transport belt, with it also being conceivable for the sample to remain in the treatment apparatus and only the empty cup going back with the sample carrier to the transport belt.

Thus, a need exists to simplify the handling of melt samples in steel production and to shorten the time for sample preparation, sample handling, and chemical analysis.

DETAILED DESCRIPTION

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The present disclosure generally relates to methods for handling melt samples in a steelworks laboratory and also to steelworks laboratories. In some examples, a melt sample is processed and/or analyzed in at least one first treatment apparatus and is subsequently transported via at least one first transport path to at least one second treatment apparatus where the melt sample is subjected to further processing and/or analysis.

In the method of the invention for handling melt samples in a steelworks laboratory, the melt sample is processed and/or analyzed in at least one first treatment apparatus and is subsequently transported via at least one first transport path to at least one second treatment apparatus where the melt sample is subjected to further processing and/or analysis. Here, the melt sample is clamped on a sample carrier so that the sample carrier is transported together with the clamped-in melt sample between the treatment apparatuses and is positioned in the treatment apparatuses for processing and/or analysis.

The sample thus remains on the sample carrier up to the last treatment apparatus, so that no reclamping and measuring and thus less handling are necessary in between. Since the sample carriers always have the same shape, in contrast to the clamped-in samples, easier handling is also provided for transfer between a transport apparatus and the treatment apparatus.

The steelworks laboratory according to the invention for handling melt samples provides at least one first and a second treatment apparatus for processing and/or analysis of the melt samples and also a transport apparatus for transporting the melt samples between the treatment apparatuses. Furthermore, a sample carrier having a first clamping device for clamping-in the melt sample is provided, with the sample carrier together with a clamped-in sample being configured for transport on the transport apparatus. In the region of the treatment stations, there is also arranged a transfer unit for transferring the sample carrier with the clamped-in melt sample into the treatment apparatus.

Further embodiments of the invention are subject matter of the dependent claims.

In one embodiment of the invention, the sample carrier is placed together with the clamped-in melt sample on a transport apparatus, which is formed by way of example by a conveyor belt or a rail system, for transport between the at least two treatment stations. However, it is also conceivable for the purposes of the invention for transport between the treatment apparatuses to occur by means of a robot. In a further embodiment, the sample carrier together with the clamped-in melt sample can be transferred between the transport apparatus and the at least one treatment apparatus, with positioning in a rotated position (180°), for example from the top, also being able to be provided in the treatment station. This can be necessary when the analyses are carried out from below and the melt sample has to be held from the top.

In particular treatments of the sample, the position and height thereof in the treatment apparatus is also of critical importance. Thus, for example, in spark emission spectroscopy (OES) the position of the sample is critically important for the analysis of the melt sample. For this purpose, the surface of the melt sample is analyzed for defects by image analysis, so that an analysis in the "clean" region of the sample surface can be carried out as a result of the unambiguous position of the melt sample on the sample carrier. The height of the sample is especially important for milling machining in a milling machine.

In a preferred embodiment of the invention, the melt sample clamped on the sample carrier is therefore measured in terms of its position and height relative to the sample carrier before the melt sample is positioned in a measurement station, so that these data can be utilized if required in the individual treatment apparatuses. Thus, in the treatment apparatuses in which precise alignment is important, renewed measurement is no longer required. In a further embodiment, the measurement data can be transmitted to at least one of the treatment stations before processing and/or analysis of the melt sample.

In the treatment apparatuses, the melt samples can optionally be subjected to cooling and/or a surface treatment and/or X-ray fluorescence analysis and/or analysis by means of spark emission spectrometry. If a surface treatment of the melt sample is carried out, the treatment apparatus can be provided with a clamping device which acts on the sample carrier positioned in the treatment apparatus in order to increase the clamping force acting on the melt sample. Such an additional clamping force is particularly advantageous in the case of a milling machine.

The melt samples and/or the associated sample carrier can be marked for identification of the melt samples; here, the associated sample carrier also records the treatment information (e.g. the measurement data) for the melt sample and transmits it to the treatment apparatuses.

In an embodiment of the invention, the first clamping device of the sample carrier has clamping jaws which are provided with a microparticle coating to increase the coefficient of friction and ensure that the sample is held securely. It is also conceivable for the sample carrier to be equipped with a second clamping device for clamping in a further melt sample, so that two melt samples can be transported together. Here, it is particularly advantageous for one melt sample to be arranged on the upper side and the other melt sample to be arranged on the underside of the sample carrier, as a result of which a relatively compact shape is obtained. In addition, the time for sample preparation, sample treatment and chemical analysis can be decreased further in this way. Overall, a time of only 2-3 minutes is desirable for these three fully automated process steps, including transport of the sample into the laboratory.

Figure 1:
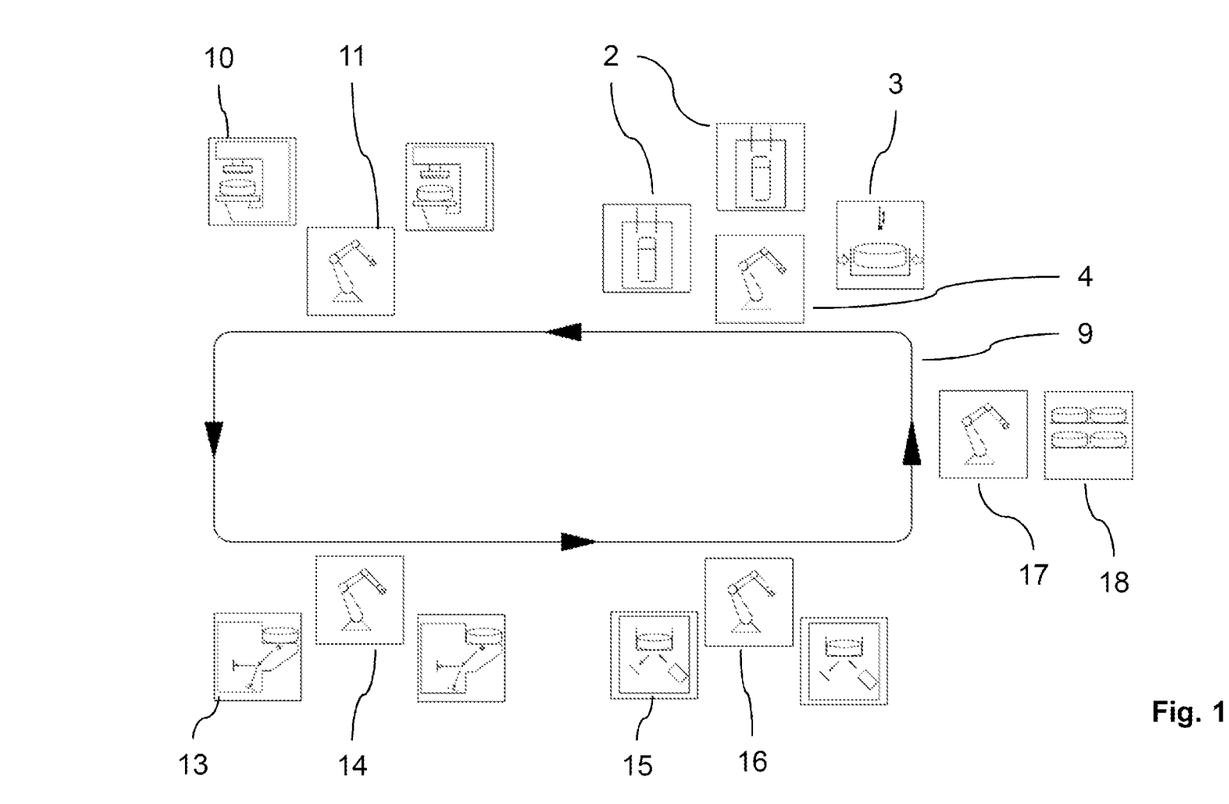
FIG. 1 is a block flow diagram of an example steelworks laboratory.

FIG. 1 shows a steelworks laboratory for sample preparation, for sample handling and for chemical analysis of melt samples from steel production. The sampling operation, which is not depicted in more detail here, is carried out by dipping special sampling probes into the melt. Depending on the probe, a distinction is made between lollipop samples, cone or chill mold samples, oval samples and bracket samples, with lollipop samples and oval samples being preferred because they can be handled automatically after the stem has been separated off.

Figure 2:
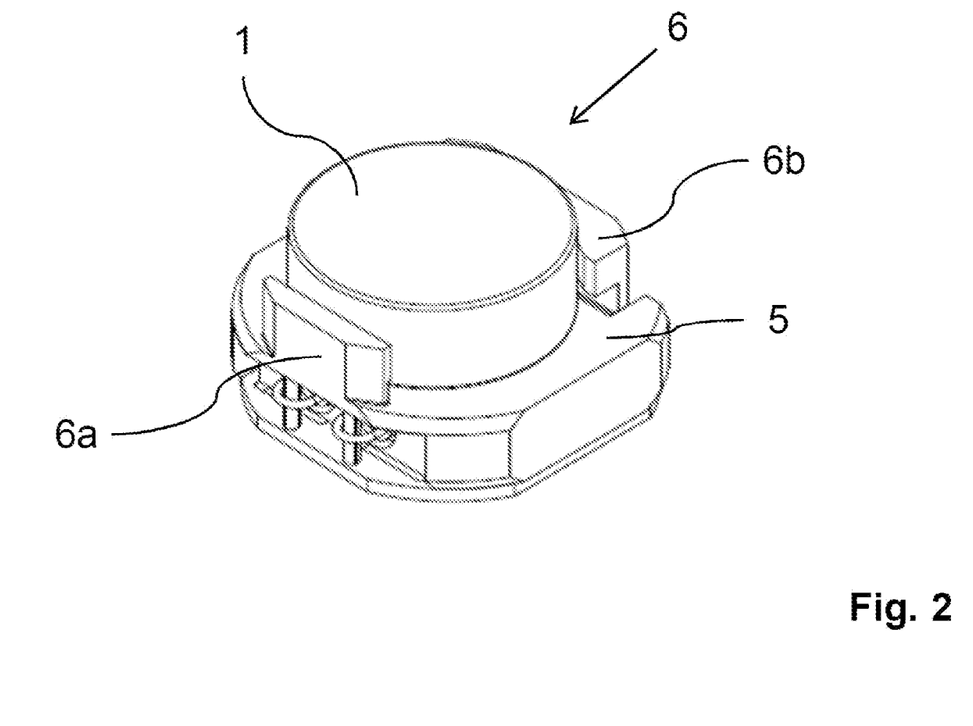
FIG. 2 is a perspective view of an example sample carrier with a clamped-in melt sample.
Figure 3:
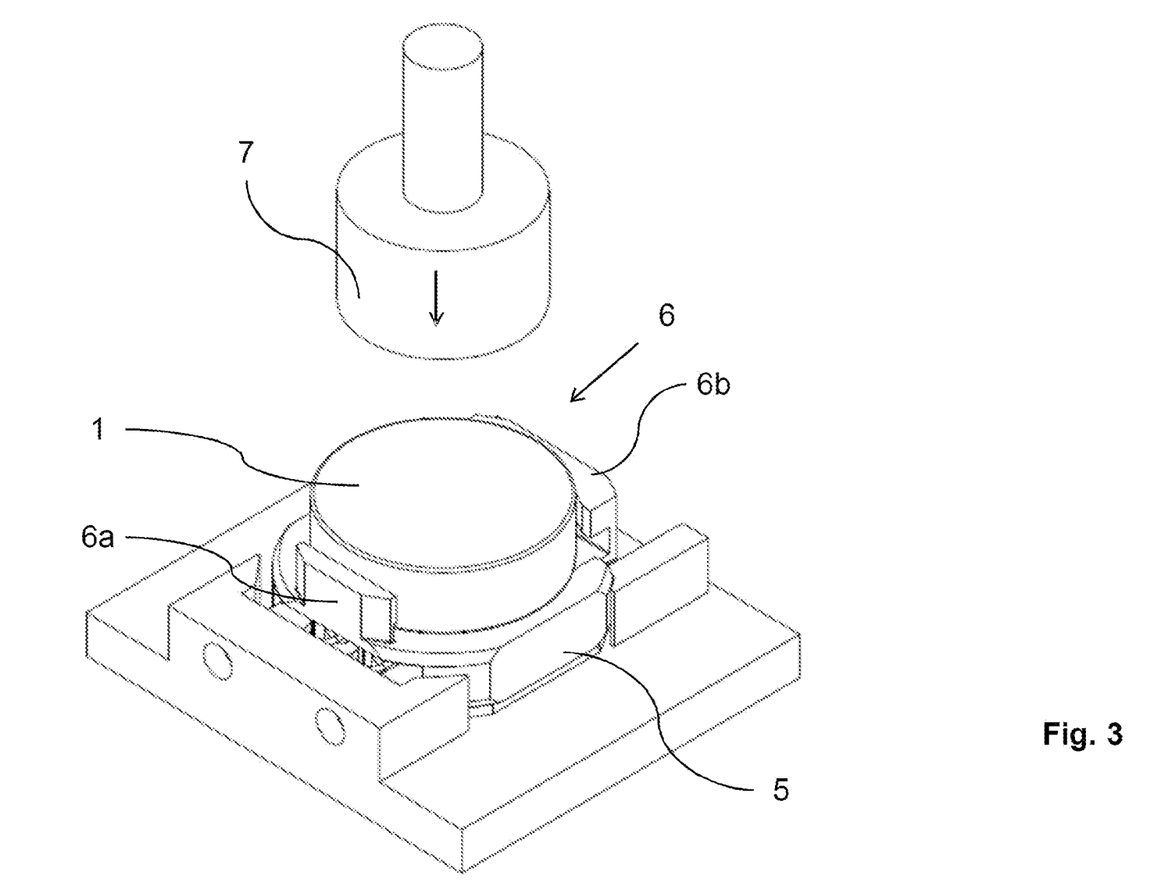
FIG. 3 is a schematic view of an example clamping and measuring device for clamping-in and measuring a melt sample.

In the vicinity of the sampling position, the melt samples 1 taken are transferred to a tube transport station and transported together with a tube transport can to the steelworks laboratory. In the steelworks laboratory, there is at least one tube transport receiver 2 which automatically opens the tube transport can and takes out the melt sample 1. The melt sample 1 is transferred to a clamping and measuring station 3, for example by means of a robot 4 (FIG. 3). As shown in FIG. 2, the melt sample is clamped onto a sample carrier 5 there. The sample carrier 5 has for this purpose a first clamping device 6 which is depicted here by a fixed clamping jaw 6a and a spring-preloaded clamping jaw 6b. The two clamping jaws 6a, 6b can be provided with a microparticle coating to increase the holding force. The melt sample 1 clamped on the sample carrier 5 is subsequently measured by means of at least one measuring device 7; in particular, the position and the height of the melt sample 1 relative to the sample carrier 5 is determined. The measurement data are either stored on the sample carrier 5, for example by means of an RFID system, or transmitted directly to the treatment apparatuses. In each, either the melt samples and/or the associated sample carriers are marked in a suitable way for identification of the melt sample 1, so that each melt sample 1 can be unambiguously identified at the respective treatment apparatuses.

Figure 4:
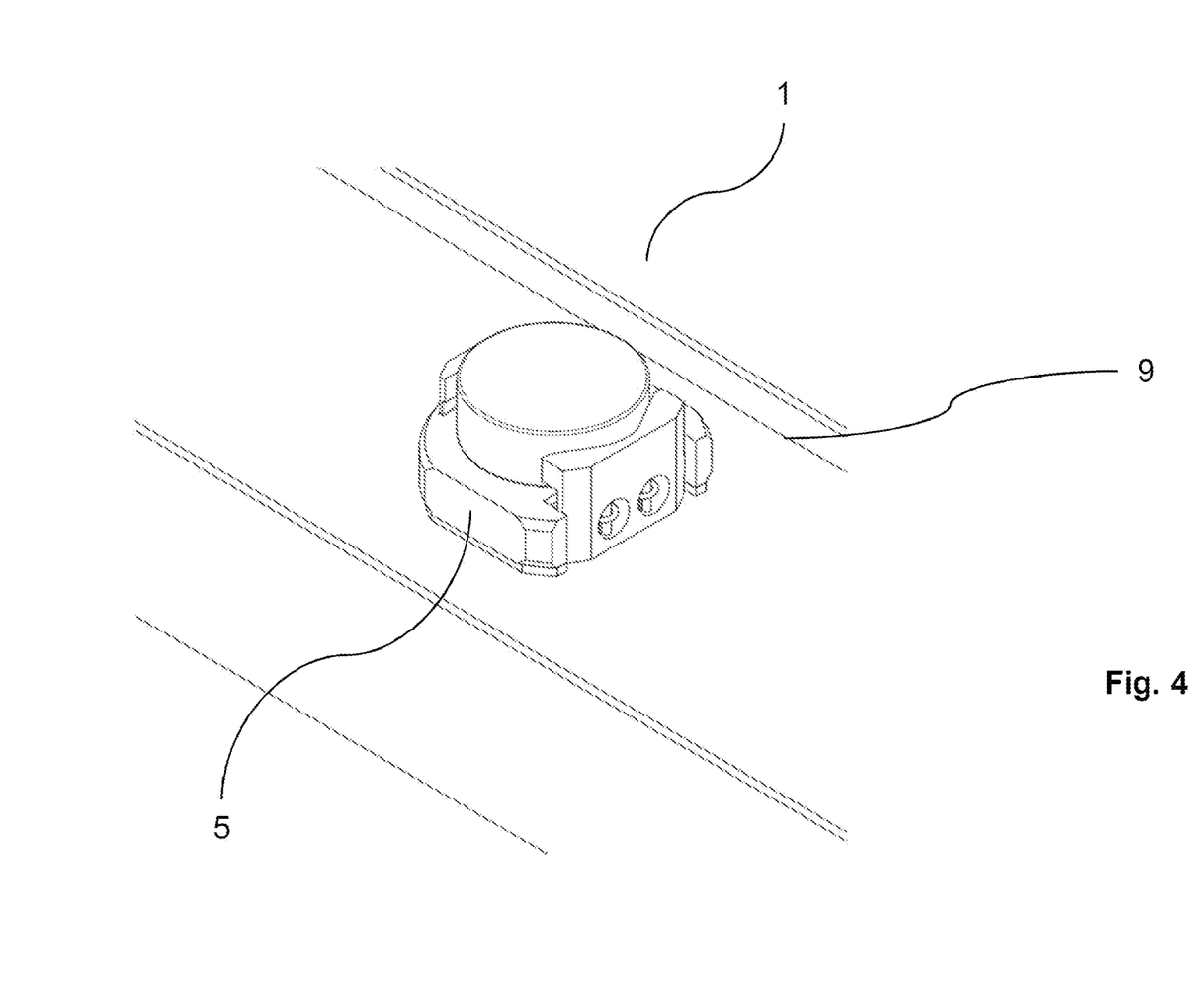
FIG. 4 is a schematic view of an example sample carrier with a clamped-in melt sample on an example transport apparatus.

The sample carrier 5 with the clamped-in melt sample 1 is moved by means of the robot 4 from the clamping and measuring station 3 and placed on a transport apparatus 9 in order to transport the sample carrier 5 to a first treatment station 10 (FIG. 4), which is in the present case a milling machine. The transfer of the transport apparatus 9 into the first treatment station 10 is effected by means of a suitable transfer device which is, for example, formed by a second robot 11. Here, the sample carrier 5 is transferred together with the clamped-in melt sample 1 into the milling machine.

Figure 5A:
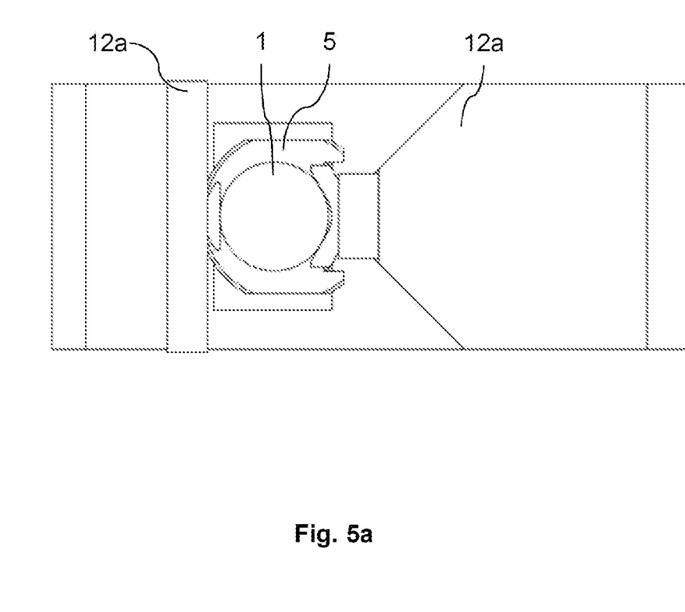
FIG. 5a is a plan view of an example clamping device in a treatment apparatus.
Figure 5B:
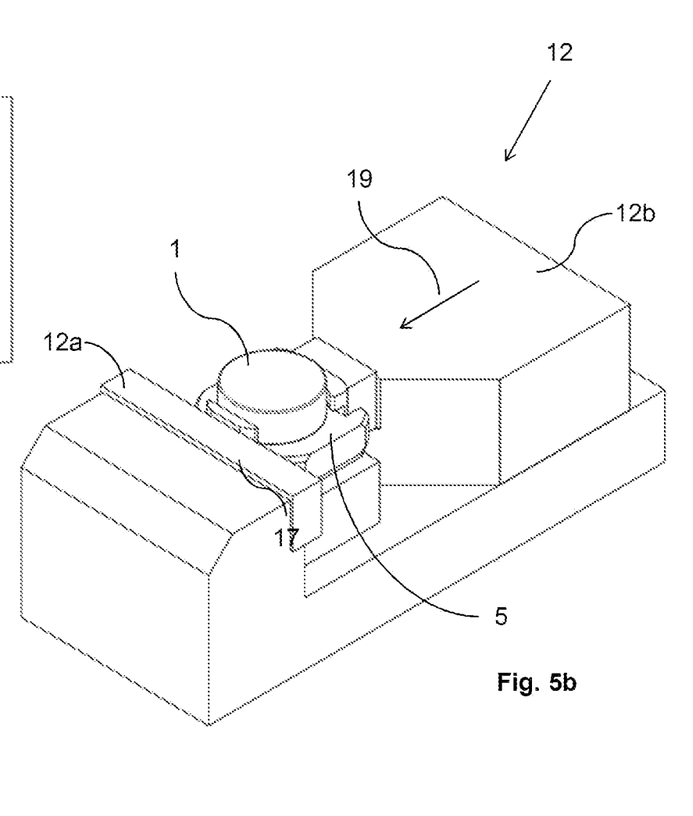
FIG. 5b is a perspective view of the clamping device of FIG. 5a in the treatment apparatus.

The uppermost layer of the melt sample is characterized by oxidation and has an about 0.5 mm thick scale layer which is not representative of the melt sample. Underneath this there is a layer having a thickness of some millimeters which is suitable for a representative analysis. The scale layer on the melt sample 1 therefore has to be removed over the entire area. For this purpose, the use of a milling machine has become established. Since increased forces act on the melt sample 1 during the milling operation, the first treatment station 10 (milling machine) has an additional clamping apparatus which in the sample carrier 5 positioned in the first treatment apparatus 10 is in operative contact with the first clamping device 6 of the sample carrier 5 in order to increase the clamping force acting on the melt sample 1 (FIGS. 5a, 5b). The clamping device 12 of the first treatment apparatus 10 consists of a fixed jaw 12a and a movable jaw 12b, with the sample carrier 5 being placed in the clamping device 12 in such a way that the fixed clamping jaw 6a of the sample carrier 5 comes into operative contact with the fixed jaw 12a and the spring-preloaded clamping jaw 6b comes into operative contact with the movable jaw 12b. The total clamping force acting on the melt sample can be increased by the additional force (arrow 19) of the movable jaw 12b and the melt sample can in this way be securely held in place even during milling.

Figure 6A:
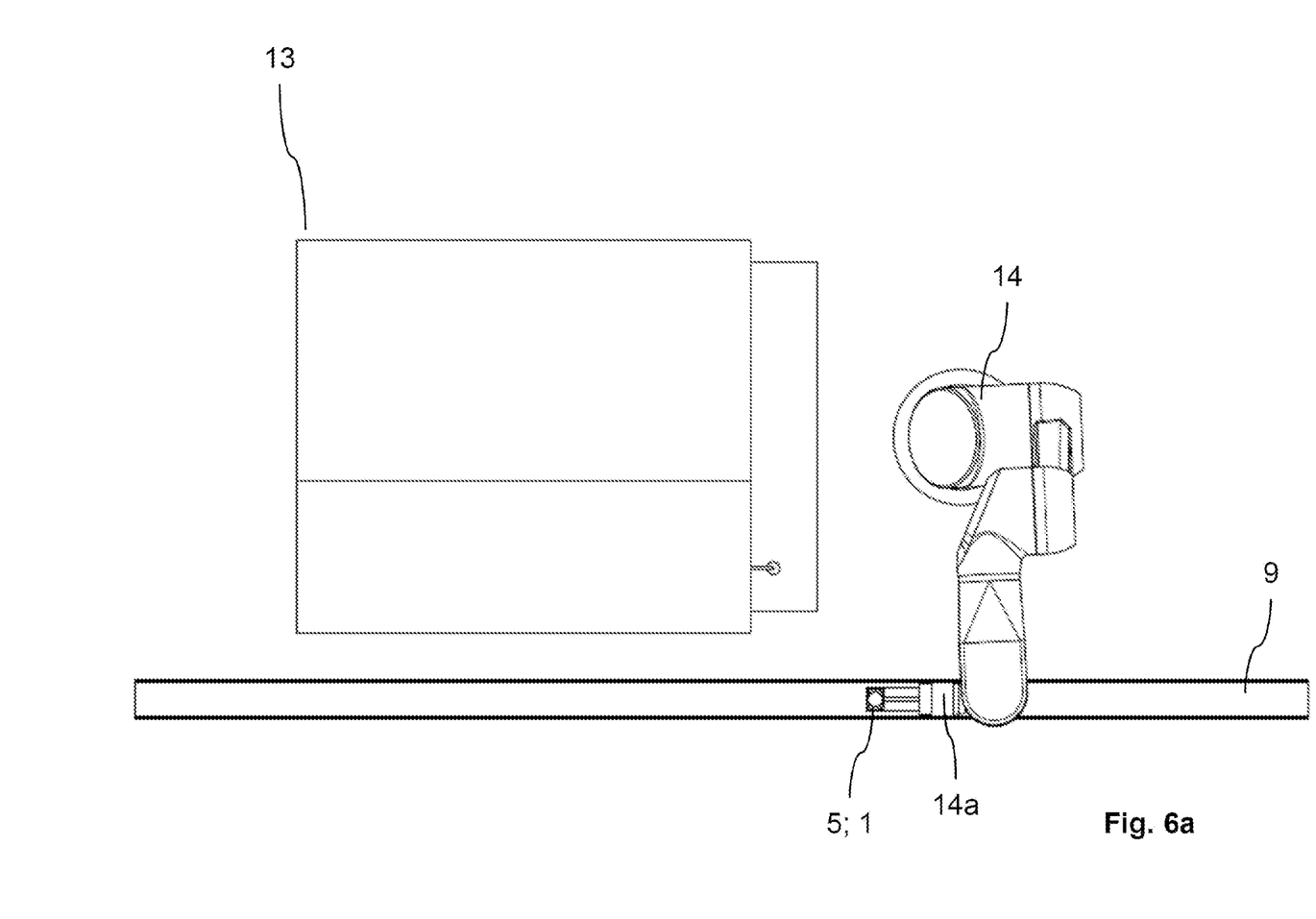
FIG. 6a is a side view illustrating transfer of a sample carrier from a transport apparatus into a treatment apparatus.
Figure 6B:
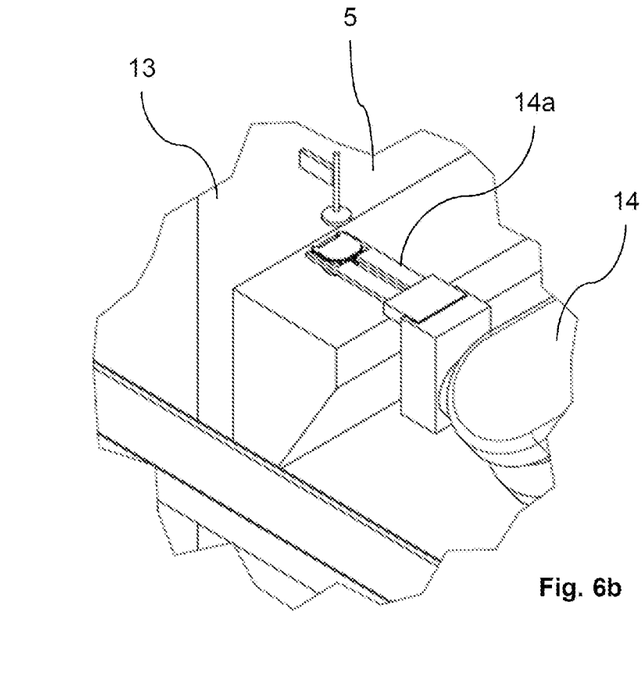
FIG. 6b is a perspective view illustrating transfer of the sample carrier from the transport apparatus into the treatment apparatus.
Figure 6C:
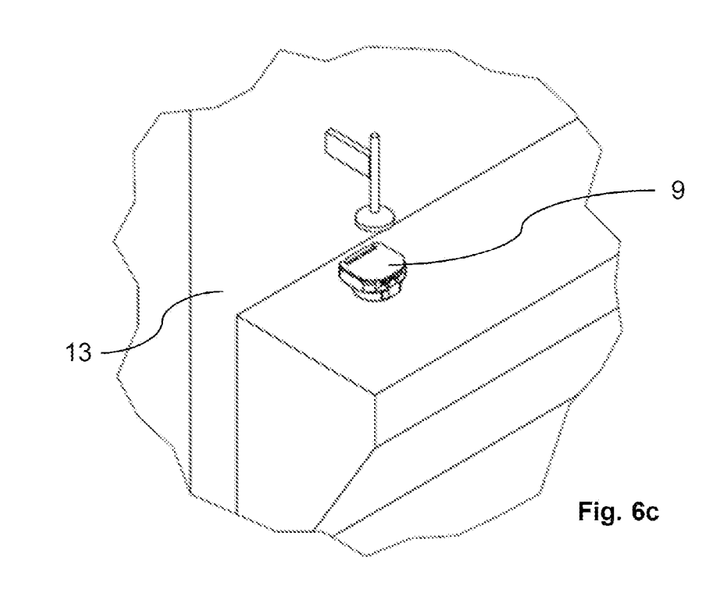
FIG. 6c is a perspective view illustrating further transfer of the sample carrier from the transport apparatus into the treatment apparatus.

After the milling work, the sample carrier 5 together with clamped-in melt sample 1 is again placed on the transport apparatus 9 by the second robot 11 in order to go to the second treatment apparatus 13. This is, for example, an instrument for spark emission spectroscopy (OES), which allows rapid chemical analysis of the melt sample 1 and presentation of the emission spectrum of chemical substances. OES analysis is, like XRF analysis, intended for qualitative and quantitative determination of the elemental composition of a sample, with the differences being in the accuracy and the analysis time. The transfer from the transport apparatus 9 into the second treatment apparatus 13 is depicted in FIGS. 6a to 6c and is here effected by a third robot 14 having a suitable grasper 14a.

An instrument for X-ray fluorescence analysis (XRF) is provided as third treatment apparatus 15; this represents a method for the qualitative and quantitative determination of the elemental composition of a sample and has the advantage that the samples are not destroyed by the measurement and no digestion steps are required. The transfer of the sample carrier 5 with the clamped-in melt sample 1 is carried out here by a fourth robot 16.

After all analyses have been carried out on the melt sample 1, the latter goes with the assistance of a fifth robot into a sample store where the melt sample is taken out from the sample carrier 5 so that the sample carrier can be used for a fresh melt sample. The transport system is therefore also advantageously configured as a continuous loop, so that the empty sample carrier next goes back to the clamping and measuring station 3.

The steelworks laboratory depicted in FIG. 1 should be regarded merely as a conceivable working example. However, other embodiments are also conceivable in the context of the invention. Thus, the individual treatment stations can also be present a number of times, especially as a function of the number of melt samples to be analyzed. It is also conceivable for a plurality of treatment stations to be arranged in the operative region of a single transfer apparatus (robot).

Figure 7:
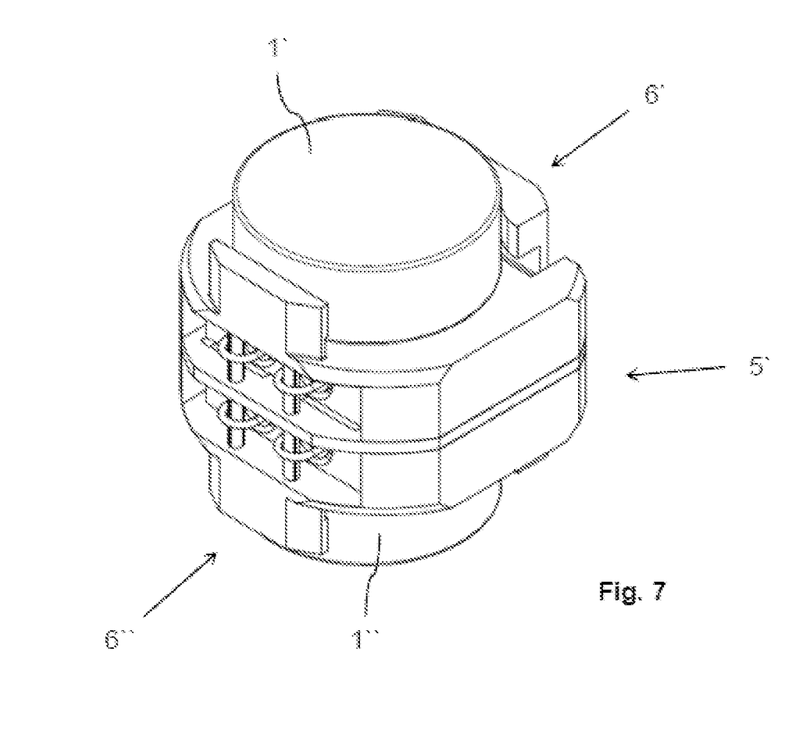
FIG. 7 is a perspective view of an example sample carrier for two melt samples.

Finally, FIG. 7 shows a second working example of a sample carrier 5' which is configured so that two melt samples 1', 1" can be accommodated. In the working example depicted, the sample carrier 5' is formed essentially by two sample carriers as per FIG. 2 being joined to one another on their side opposite the clamped-in melt sample, so that a first melt sample 1' can be clamped in at the top and a second melt sample 1" can be clamped in at the bottom, in each case using separate clamping devices 6', 6". In this way, two melt samples can be transported at the same time and the treatment in the treatment apparatuses can also occur more quickly since the sample carrier 5' merely has to be turned over by the transfer apparatus (robot).

What is claimed is:

1. A method for handling melt samples in a steelworks laboratory, the method comprising:
   processing and/or analyzing a melt sample in a first treatment apparatus;
   transporting the melt sample after the processing and/or analyzing via a first transport path to a second treatment apparatus where the melt sample is further processed and/or analyzed, wherein the melt sample is clamped on a sample carrier and transported with the sample carrier between the first and second treatment apparatuses and is positionable in the first and second treatment apparatuses for the respective processing and/or analyzing; and
   further comprising at least one of cooling, surface treating, performing X-ray fluorescence analysis, or analyzing by spark emission spectrometry in either the first or second treatment apparatuses.

2. The method of claim 1 wherein the sample carrier together with the clamped-in melt sample is placed on a transport apparatus for transport between the first and second treatment apparatuses.

3. The method of claim 2 wherein the sample carrier together with the clamped-in melt sample are transferred from the transport apparatus into each of the first and second treatment apparatuses.

4. The method of claim 3 wherein the sample carrier together with the clamped-in melt sample are positioned in a rotated position during transfer between the transport apparatus and the first or second treatment apparatus.

5. The method of claim 3 wherein the sample carrier together with the clamped-in melt sample are positioned in a rotated position in a transfer unit during transfer between the transport apparatus and the first or second treatment apparatus.

6. The method of claim 1 comprising:
   measuring the melt sample clamped on the sample carrier in terms of position and height relative to the sample carrier before positioning the melt sample in the first or second treatment apparatus; and transmitting measurement data to the first or second treatment apparatus before processing and/or analyzing of the melt sample in the respective first or second treatment apparatus.

7. The method of claim 1 comprising:

surface treating the melt sample in at least one of the first and second treatment apparatuses; and providing a clamping device in the at least one of the first and second treatment apparatuses that acts on the sample carrier positioned in the at least one of the first and second treatment apparatuses to increase a clamping force acting on the melt sample.

8. The method of claim 1 comprising marking at least one of the melt sample or the sample carrier to identify the melt sample.

9. The method of claim 8 wherein the sample carrier records treatment information regarding the melt sample and transmits the treatment information to the first and second treatment apparatuses.

* * * * *